United States Patent
Shoji

(10) Patent No.: US 8,366,786 B2
(45) Date of Patent: Feb. 5, 2013

(54) ARTIFICIAL BONE CAPABLE OF BEING ABSORBED AND REPLACED BY AUTOGENOUS BONE AND ITS PRODUCTION METHOD

(75) Inventor: Daisuke Shoji, Tokyo (JP)

(73) Assignee: Hoya Corporation, Tokyo (JP)

( * ) Notice: Subject to any disclaimer, the term of this patent is extended or adjusted under 35 U.S.C. 154(b) by 60 days.

(21) Appl. No.: 12/631,931

(22) Filed: Dec. 7, 2009

(65) Prior Publication Data

US 2010/0145468 A1    Jun. 10, 2010

(30) Foreign Application Priority Data

Dec. 9, 2008 (JP) ................................. 2008-313340

(51) Int. Cl.
  A61F 2/36   (2006.01)
  A61F 2/28   (2006.01)
(52) U.S. Cl. .................... 623/23.51; 623/16.11
(58) Field of Classification Search ............... 623/16.11, 623/23.51
  See application file for complete search history.

(56) References Cited

U.S. PATENT DOCUMENTS

| 7,153,938 | B2 | 12/2006 | Kikuchi et al. | |
| 2001/0039455 | A1* | 11/2001 | Simon et al. | 623/23.51 |
| 2003/0236573 | A1 | 12/2003 | Evans et al. | |
| 2004/0249463 | A1* | 12/2004 | Bindseil et al. | 623/17.16 |
| 2008/0249637 | A1* | 10/2008 | Asgari | 623/23.72 |
| 2010/0166828 | A1 | 7/2010 | Shoji | |

OTHER PUBLICATIONS

Written Opinion issued with respect to French Application No. FR0958788, mailed Dec. 21, 2010.
Kikuchi et al., "Fabrication of Interconnected Porous Material Using Hydroxyapatite/Collagen Nanocomposite Membrane" Annual Meeting of The Ceramic Society of Japan, (Mar. 20-22, 2008), Conference Proceedings, p. 324, including a partial English language translation.
U.S. Appl. No. 12/647,011 to Shoji, D., entitled "Artificial Bone Capable of Being Absorbed and Replaced by Autogenous Bone and Its Production Method" filed Dec. 24, 2009.
English translation of a Written Opinion issued with respect to French Application No. FR0958788, mailed Dec. 21, 2010.

* cited by examiner

Primary Examiner — Thomas J Sweet
Assistant Examiner — Jason-Dennis Stewart
(74) Attorney, Agent, or Firm — Greenblum & Bernstein, P.L.C.

(57) ABSTRACT

An artificial bone capable of being absorbed and replaced by an autogenous bone, which comprises a cylindrical body obtained by rolling a sheet-shaped apatite/collagen composite, a hollow center portion of the cylindrical body penetrating from one end surface to the other end surface having a diameter of 100-1000 μm.

6 Claims, 1 Drawing Sheet

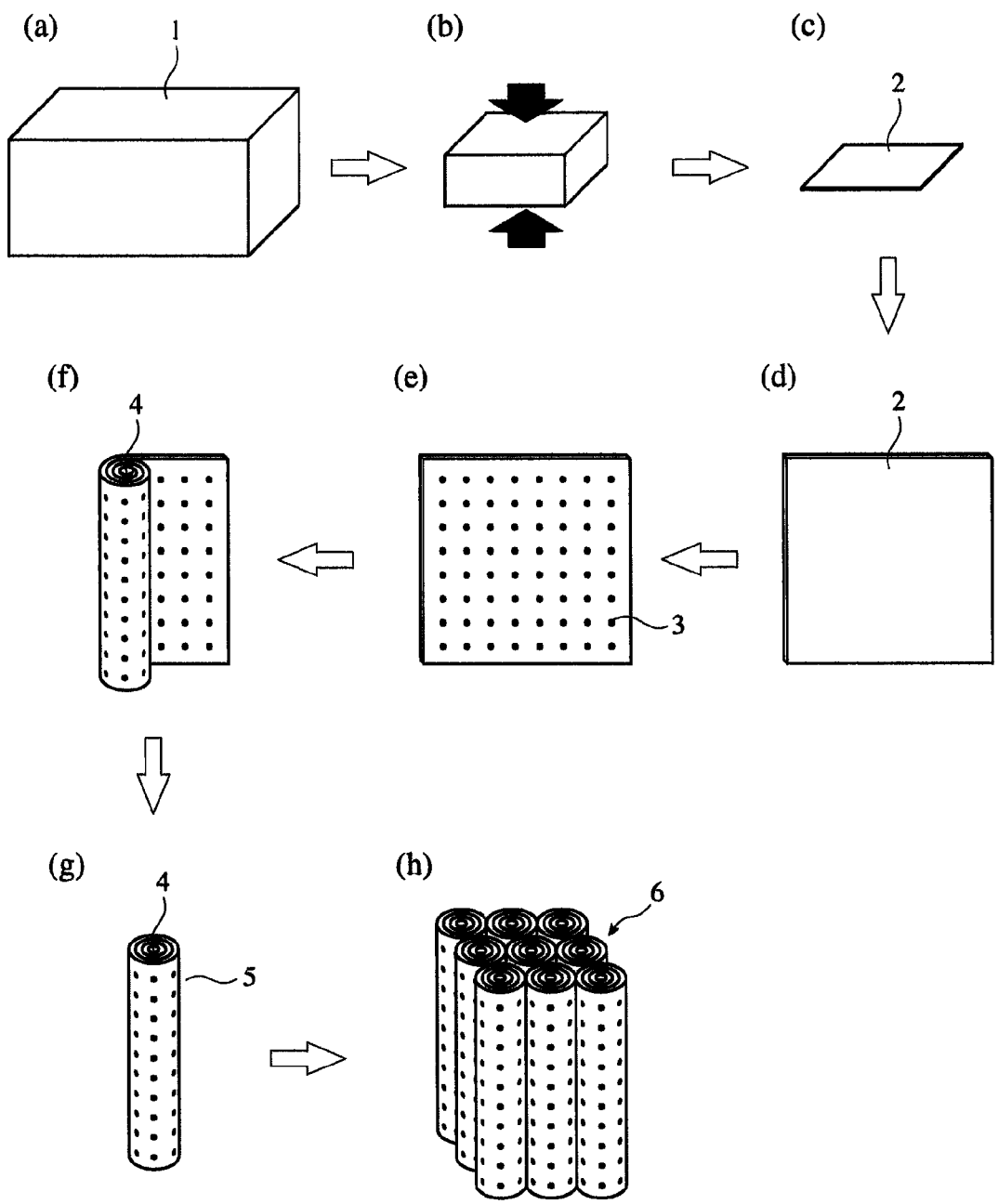

ARTIFICIAL BONE CAPABLE OF BEING ABSORBED AND REPLACED BY AUTOGENOUS BONE AND ITS PRODUCTION METHOD

FIELD OF THE INVENTION

The present invention relates to an artificial bone having mechanical properties on the same level as those of living bones, which is absorbed and replaced by an autogenous bone when implanted in the body, and its production method.

BACKGROUND OF THE INVENTION

Used for the treatment of bone defects caused by injuries or diseases are the transplantation of an autogenous bone taken from a patient himself, the transplantation of a similar bone taken from another person, the implanting of an artificial bone made of a metal such as titanium or hydroxyapatite ceramics, etc. Hydroxyapatite ceramics can directly bond to bones because of bone conduction which is not owned by conventional metals, polymers and alumina ceramics. Therefore, they have been gradually finding applications as bone-repairing materials substituting for autogenous bones in wide regions such as oral surgery, neurological surgery, oto-rhino-laryngology, orthopedic surgery, etc. However, artificial bones of ceramics typified by hydroxyapatite are disadvantageously difficult to handle during operation because they are hard and brittle. To overcome this problem, a spongy, elastic apatite/collagen composite was developed. Although this material is easily handled, it cannot be used alone in a body portion subjected to stress because of low mechanical strength.

Resume of Lectures in 2008 Annual Meeting of The ceramic Society of Japan, page 324, lower column discloses a permeable, porous, cylindrical body, which is formed by rolling a wave-sheet-shaped hydroxyapatite/collagen nano-composite. This reference describes that this permeable, porous body has excellent tissue penetrability and bone conduction, because it has a hollow center portion similar to a relatively large medullary cavity, and penetrating pores formed on a peripheral surface to permit cells and tissues to enter. However, because this penetrable, porous body is formed by a wave-sheet-shaped composite and has a hollow portion similar to a relatively large medullary cavity, it has disadvantageously low strength despite excellent tissue penetrability and bone conduction.

OBJECTS OF THE INVENTION

Accordingly, an object of the present invention is to provide an artificial bone having mechanical properties on the same level as those of living bones as well as excellent tissue penetrability and bone conduction, which is absorbed (biodegraded) and replaced by an autogenous bone when implanted in the body.

Another object of the present invention is to provide a method for producing such an artificial bone.

DISCLOSURE OF THE INVENTION

As a result of intensive research in view of the above objects, the inventors have found that a cylindrical body obtained by rolling a sheet-shaped apatite/collagen composite sheet provided with a large number of pores has sufficient strength as well as excellent tissue penetrability and bone conduction. The present invention has been completed based on such finding.

The artificial bone capable of being absorbed and replaced by an autogenous bone according to the present invention comprises a cylindrical body obtained by rolling a sheet-shaped apatite/collagen composite, a hollow center portion of the cylindrical body penetrating from one end surface to the other end surface having a diameter of 100-1000 µm.

The sheet-shaped apatite/collagen composite preferably has pores having diameters of 100-1000 µm at a density of 1 or more per 1 $cm^2$.

The artificial bone capable of being absorbed and replaced by an autogenous bone according to the present invention is preferably obtained by bundling pluralities of the cylindrical apatite/collagen composites.

The method of the present invention for producing an artificial bone capable of being absorbed and replaced by an autogenous bone, which comprises a cylindrical apatite/collagen composite, comprises the steps of forming a sheet-shaped apatite/collagen composite, and rolling the sheet-shaped apatite/collagen composite into a cylindrical body.

The sheet-shaped apatite/collagen composite is preferably formed by compressing a block-shaped apatite/collagen composite.

The method of the present invention for producing an artificial bone capable of being absorbed and replaced by an autogenous bone preferably further comprises the step of providing the sheet-shaped apatite/collagen composite with pores having diameters of 100-1000 µm.

The method of the present invention for producing an artificial bone capable of being absorbed and replaced by an autogenous bone preferably further comprises the step of bundling pluralities of cylindrical apatite/collagen composites.

Pluralities of the cylindrical apatite/collagen composites are preferably cross-linked after bundled.

BRIEF DESCRIPTION OF THE DRAWINGS

FIG. 1 is a schematic view showing one example of the procedures for producing the artificial bone of the present invention.

DESCRIPTION OF THE PREFERRED EMBODIMENTS

FIG. 1 shows a method for producing the artificial bone of the present invention. A sheet-shaped apatite/collagen composite can be obtained, for instance, by compressing a porous body 1 [FIG. 1(a)] of the apatite/collagen composite described in US 2005/0271695 A1 (corresponding to WO 2004/041320 A1) with a monoaxial press, etc. to form a sheet 2 [FIGS. 1(b) to 1(d)] before cross-linking. A weight ratio of apatite to collagen is preferably 9/1 to 2/8 from the aspect of tensile strength. The sheet 2 is preferably provided with pores 3 of 100-1000 µm in diameter by punching, etc. in advance [FIG. 1(e)]. This sheet 2 is preferably rolled [FIG. 1(f)] into a cylindrical body 5 of the apatite/collagen composite having a hollow center portion 4 of 100-1000 µm in diameter [FIG. 1(g)]. Although a cylindrical apatite/collagen composite may be used alone as an artificial bone, pluralities of the cylindrical bodies are preferably bundled to form an artificial bone 6 [FIG. 1(h)]. Cross-linking is preferably conducted after rolling the sheet 2 into a cylindrical body 5, or after bundling pluralities of cylindrical bodies 5. To increase the density of the apatite/collagen composite, the apatite/collagen composite may be compressed before cross-linking, if necessary. The artificial bone 6 may be obtained by integrally rolling a sheet 2 around pluralities of bundled cylindrical bodies. The sheet 2 rolled around pluralities of bundled cylindrical bodies preferably has pores 5.

[1] Production of Porous Apatite/Collagen Composite

The porous apatite/collagen composite is constituted by pluralities of layers of apatite/collagen composite fibers. The fiber layers have planar shapes as thick as about 10-500 μm and overlapped in random directions with random numbers. Disposed sparsely between the fiber layers are pillars composed of the apatite/collagen composite fibers. Because only sparsely arranged pillars support the fiber layers in an overlapping direction when viewed microscopically, it may be considered that the porous apatite/collagen composite is relatively brittle in the overlapping direction, while it has high strength in a layer direction. However, because the fiber layers are overlapping in random directions as described above, the overlapping directions of the fiber layers are averaged when viewed macroscopically, resulting in little anisotropy of strength.

Substantially planar-shaped pores are formed between the fiber layers with pillars. The thickness of the substantially planar-shaped pores is about 0.5-10 times that of the fiber layers. When this porous apatite/collagen composite is embedded in the body, it is considered that blood vessels, relatively large proteins, etc. easily enter substantially planar pores, accelerating bone formation. Incidentally, the pore shape is not restricted to be planar, but may be spherical.

(1) Apatite/Collagen Composite Fibers (a) Starting Materials

The apatite/collagen composite fibers are formed from starting materials comprising collagen, phosphoric acid or its salts, and calcium salts. Though not particularly restrictive, the collagen may be extracted from animals, etc. The kinds, parts, ages, etc. of the animals to be extracted are not particularly restrictive. Generally usable are collagen obtained from skins, bones, cartilages, tendons, internal organs, etc. of mammals such as cow, pig, horse, rabbit and rat and birds such as hen, etc. Collagen-like proteins obtained from skins, bones, cartilages, fins, scales, internal organs, etc. of fish such as cod, flounder, flatfish, salmon, trout, tuna, mackerel, red snapper, sardine, shark, etc. may also be used. The extraction method of collagen is not particularly restrictive but may be a usual one. In place of collagen extracted from animal tissues, collagen produced by gene recombination technologies may also be used.

The phosphoric acid or its salt [simply called "phosphoric acid (salt)"] may be phosphoric acid, disodium hydrogenphosphate, sodium dihydrogenphosphate, dipotassium hydrogenphosphate, potassium dihydrogenphosphate, etc. The calcium salts may be calcium carbonate, calcium acetate, calcium hydroxide, etc. The phosphoric acid (salt) and the calcium salt are preferably added in the form of a uniform aqueous solution or suspension.

The mass ratio of apatite to collagen in the resultant apatite/collagen composite fibers can be controlled by a mass ratio of the apatite-forming materials [phosphoric acid (salt) and calcium salt] to collagen used. Accordingly, the mass ratio of the apatite-forming materials to collagen is properly determined depending on a targeted composition of the apatite/collagen composite fibers. The mass ratio of apatite to collagen in the apatite/collagen composite fibers is preferably 9/1 to 2/8, for instance, about 8/2.

(b) Preparation of Solution

Though the concentrations of the aqueous phosphoric acid (salt) solution and the aqueous calcium salt solution are not particularly restrictive as long as the phosphoric acid (salt) and the calcium salt are at a desired ratio, it is preferable for the convenience of a dropping operation described later that the concentration of the aqueous phosphoric acid (salt) solution is about 50-250 mM, and that the concentration of the aqueous calcium salt solution is about 200-600 mM. Collagen is generally added in the form of an aqueous solution in phosphoric acid to the aqueous phosphoric acid (salt) solution in advance. The aqueous solution of collagen in phosphoric acid preferably contains collagen at a concentration of 0.5-1% by mass, and phosphoric acid at a concentration of 10-30 mM. More preferably, the collagen concentration is 0.8-0.9% by mass, and the phosphoric acid concentration is 15-25 mM. Particularly, the collagen concentration is about 0.85% by mass, and the phosphoric acid concentration is about 20 mM.

(c) Production Method

Water substantially in the same amount as that of the aqueous calcium salt solution to be added, preferably in an amount of 0.5-2 times, more preferably 0.8-1.2 times, that of the aqueous calcium salt, is charged into a reaction vessel and heated to about 40° C. in advance. An aqueous phosphoric acid (salt) solution containing collagen and an aqueous calcium salt solution are simultaneously dropped thereinto. The length of the synthesized apatite/collagen composite fibers can be controlled depending on dropping conditions. The dropping speed is preferably about 10-50 ml/minute, and the stirring speed of a reaction solution is preferably about 50-300 rpm. To keep the reaction solution at pH of 8.9 to 9.1, it is preferable to keep the concentration of calcium ions at 3.75 mM or less and the concentration of phosphoric acid ions at 2.25 mM or less in the reaction solution during dropping. If the concentrations of calcium ions and/or phosphoric acid ions exceeded the above ranges, the self-organization of the composite would be hindered. The above dropping conditions provide the self-organized apatite/collagen composite fibers as long as 1 mm or less suitable for the porous body. The term "self-organization" used herein means that hydroxyapatite (calcium phosphate having an apatite structure), namely the C-axis of hydroxyapatite, is oriented along the collagen fibers peculiarly to living bones.

After completion of dropping, a slurry-like dispersion of the apatite/collagen composite fibers is freeze-dried. The freeze-drying is carried out rapidly while evacuating in a frozen state at −10° C. or lower.

(2) Preparation of Dispersion of Apatite/Collagen Composite Fibers

The apatite/collagen composite fibers are mixed with a liquid such as water, an aqueous phosphoric acid solution, etc., and stirred to prepare a paste-like dispersion (slurry). The amount of the liquid added is preferably 80 to 99% by volume, more preferably 90 to 97% by volume, while the amount of composite fibers is preferably 1-20% by volume, more preferably 3-10% by volume. Steam is preferably attached to the apatite/collagen composite fibers in advance. In this case, the amount of the liquid added should be determined by subtracting the amount of steam attached to the apatite/collagen composite fibers.

The resultant porous body has a porosity P (%), which depends on a volume ratio of the apatite/collagen composite fibers to the liquid in the dispersion as represented by the following formula (1):

$$P = Y/(X+Y) \times 100 \tag{1},$$

wherein X represents the volume of the apatite/collagen composite fibers in the dispersion, and Y represents the volume of the liquid in the dispersion. Accordingly, it is possible to control the porosity P of the porous body by adjusting the amount of the liquid added. The apatite/collagen composite fibers are cut by stirring the dispersion after adding the liquid, resulting in a larger fiber length distribution range, and thus providing the resultant porous body with improved strength.

After adding collagen functioning as a binder to the composite dispersion, further stirring is conducted. The amount of collagen added is preferably 1-10% by mass, more preferably 3-6% by mass, based on 100% by mass of the apatite/collagen composite fibers. As in the production of the apatite/collagen composite fibers, the collagen is added preferably in the form of an aqueous solution in phosphoric acid. Though not particularly restricted, the concentration of collagen in the aqueous phosphoric acid solution is practically 0.8-0.9% by mass (for instance, 0.85% by mass), and the concentration of phosphoric acid is 15-25 mM (for instance, 20 mM).

(3) Gelation of Dispersion

An aqueous sodium hydroxide solution is added to a dispersion turned acidic by the addition of an aqueous solution of collagen in phosphoric acid (salt) to adjust its pH to about 7. The pH of the dispersion is preferably 6.8-7.6, more preferably 7.0-7.4. With the dispersion adjusted to pH 6.8-7.6, the fibrization of collagen added as a binder can be accelerated.

A phosphoric acid buffer solution (PBS) as concentrated as about 2.5-10 times is added to the dispersion and stirred to adjust its ion strength to 0.2-0.8. With the dispersion having increased ion strength, the fibrization of collagen added as a binder can be accelerated.

The dispersion charged into a molding die is kept at a temperature of 35-43° C. for gelation. The heating temperature is more preferably 35-40° C. For sufficient gelation of the dispersion, the heating time is preferably 0.5 to 3.5 hours, more preferably 1 to 3 hours. With the dispersion kept at 35-43° C., the collagen added as a binder forms fibers, thereby turning the dispersion to a gel. The gelled dispersion can prevent the apatite/collagen composite fibers from precipitating therein, thereby producing a uniform porous body.

(4) Freeze-Drying of Gel

A gel containing the apatite/collagen composite fibers is frozen. The average pore size of a porous apatite/collagen body depends on the freezing time of the gel. The freezing temperature is preferably −100° C. to 0° C., more preferably −100° C. to −10° C., particularly −80° C. to −20° C. The freezing temperature of lower than −100° C. provides the resultant porous apatite/collagen body with too small an average pore size. The temperature of higher than 0° C. fails to freeze the gel, or provides the porous body with too large an average pore size.

The frozen gel is freeze-dried to a porous body. Namely, as in the apatite/collagen composite fibers, the gel in a frozen state at −10° C. or lower is rapidly dried by evacuation. The freeze-drying time is not particularly restricted as long as the dispersion is sufficiently dried, but it is generally about 24-72 hours.

[2] Production of Sheet-Shaped Apatite/Collagen Composite

A block-shaped, porous apatite/collagen composite before cross-linking is compressed by a monoaxial press, etc. to a sheet shape. The compression ratio of the porous body is preferably 1-20%, more preferably 3-15%, most preferably 5-12%. The term "compression ratio" used herein means a $(T_1/T_0) \times 100\%$, wherein $T_0$ represents the thickness of the porous body before compression, and $T_1$ represents the thickness of the porous body after compression. The thickness of the compressed sheet is preferably 0.1-5 mm, more preferably 0.1-3 mm, most preferably 0.2-1 mm. The compression pressure is preferably 1-10000 kg/cm², more preferably 100-1000 kg/cm². The compression time is preferably 1-30 minutes. Heating to 30° C. to 40° C. may be conducted during compression.

To increase the penetrability of tissues into the artificial bone, the sheet is preferably provided with pores of 100-1000 µm in diameter in advance. Though not particularly restricted, the pores may be formed by punching, etc. The density of the pores is preferably 1 or more, more preferably 4-99, most preferably 9-49, per 1 cm² of the sheet. The pores are preferably distributed uniformly in the entire sheet.

[3] Production of Cylindrical Apatite/Collagen Composite

A sheet-shaped apatite/collagen composite cut to a proper size is rolled into a cylindrical body. Though not particularly restricted, the sheet is preferably rolled around a core rod made of Teflon (registered trademark), etc. With the core rod, the sheet can be easily rolled, and the diameter of a hollow center portion in the resultant cylindrical body can be controlled. An end of the sheet rolled into a cylindrical body may be fixed with a small amount of water or an aqueous collagen solution, but it is preferably fixed by a physical means such as press-bonding, etc. to prevent the intrusion of bacteria, etc.

A hollow center portion penetrating the cylindrical body has a diameter of preferably 100-1000 µm, more preferably 200-700 µm, most preferably 200-500 µm. The length of the cylindrical body is preferably 8-1000 mm, more preferably 10-500 mm, most preferably 10-100 mm The diameter of the cylindrical body is preferably 0.5-5 mm, more preferably 1-3 mm. It is considered that a hollow center portion having a diameter within the above range provides artificial bones having high strength and excellent tissue penetrability and bone conduction. Namely, it is considered that because the hollow center portion has a diameter of 100-1000 µm, the cylindrical body is free from such problems as poor penetrability of cells affecting the formation of bones, which may occur when the diameter of the hollow center portion is less than 100 µm, and poor bone formation due to the intrusion of fibrous tissues, which may occur when the diameter of the hollow center portion is more than 1000 µm.

[4] Production of Artificial Bone

The resultant cylindrical body may be used alone as an artificial bone, but pluralities of cylindrical bodies may be bundled to form an artificial bone. The number of cylindrical bodies bundled is preferably 10-1250, more preferably 13-25, though variable depending on the diameter of a cylindrical apatite/collagen composite and a site where the artificial bone is used. Although an artificial bone obtained by bundling pluralities of cylindrical bodies may have any shape, it is preferably in a circular or rectangular shape. To obtain an artificial bone having a desired size (diameter), the number of turns of the sheet rolled or the number of cylindrical bodies bundled may be adjusted. In the latter case, the artificial bone comprising pluralities of bundled cylindrical bodies has pluralities of hollow center portions, so that the flowing of a body liquid increases when embedded in the body, resulting in accelerated bone formation. Further, pluralities of bundled cylindrical bodies extremely increase the resistance of the cylindrical body to an axial load.

When an artificial bone is formed by only one cylindrical body, a cylindrical apatite/collagen composite is cross-linked to form an integral cylindrical body in which collagen is cross-linked to each other. When an artificial bone is formed by pluralities of bundled cylindrical bodies, temporarily bundled cylindrical bodies are cross-linked to make pluralities of cylindrical bodies integral to each other. Collagen can be cross-linked by physical cross-linking methods using γ-rays, ultraviolet rays, electron beams, thermal dehydration, etc., or chemical cross-linking methods using cross-linking agents, condensation agents, etc.

The chemical cross-linking method is conducted by immersing the apatite/collagen composite in a cross-linking agent solution. The cross-linking agents may be aldehydes such as glutaraldehyde, formaldehyde, etc.; isocyanates such as hexamethylene diisocyanate, etc.; carbodiimides such as a hydrochloric acid salt of 1-ethyl-3-(3-dimethylaminopropyl) carbodiimide; epoxies such as ethylene glycol diethyl ether, etc.; transglutaminase, etc. Among these cross-linking agents, glutaraldehyde is particularly preferable from the aspects of the easiness of controlling the degree of cross-linking and the compatibility of the cross-linked apatite/collagen composite with a living body.

When glutaraldehyde is used as the cross-linking agent, the concentration of a glutaraldehyde solution is preferably 0.005 to 0.015% by mass, more preferably 0.005 to 0.01% by mass. When alcohol such as ethanol, etc. is used as a solvent for a glutaraldehyde solution, dehydration can be conducted simultaneously with the cross-linking of collagen. To remove unreacted glutaraldehyde, the cross-linked apatite/collagen composite is immersed in an aqueous glycine solution having a concentration of about 2% by mass, and then washed with water. Further, the cross-linked apatite/collagen composite is immersed in alcohol such as ethanol for dehydration, and then dried at room temperature.

The thermal dehydration cross-linking is conducted by keeping the apatite/collagen composite in a vacuum oven at 100° C. to 160° C. and 0-100 hPa for 10-12 hours.

The present invention will be explained in further detail by Examples below without intention of restricting the present invention thereto.

Example 1

(A) Synthesis of Apatite/Collagen Composite 235 g of an aqueous solution of collagen in phosphoric acid (collagen concentration: 0.85% by mass, and phosphoric acid concentration: 20 mM) was added to 168 ml of a 120-mM aqueous phosphoric acid solution and stirred, to prepare a diluted aqueous solution of collagen in phosphoric acid. Further, 200 ml of a 400-mM calcium hydroxide suspension was prepared. 200 ml of pure water was introduced into a reaction vessel and heated to 40° C. The diluted aqueous solution of collagen in phosphoric acid and the calcium hydroxide suspension were simultaneously dropped into this reaction vessel both at a speed of about 30 ml/minute, and the resultant reaction solution was stirred at 200 rpm to prepare slurry containing apatite/collagen composite fibers. The reaction solution was kept at pH of 8.9-9.1 during dropping. The resultant apatite/collagen composite fibers were substantially as long as 1 mm or less. The slurry containing apatite/collagen composite fibers was freeze-dried. An apatite/collagen ratio in the apatite/collagen composite fibers was 8/2 on a mass basis.

(B) Production of Porous Apatite/Collagen Composite 1 g of the freeze-dried apatite/collagen composite was mixed with 3.6 ml of pure water, and stirred to prepare a paste-like dispersion. This paste-like dispersion was mixed with 4 g of an aqueous solution of collagen in phosphoric acid and stirred, and a 1-N aqueous NaOH solution was added until the pH of the dispersion became substantially 7. A ratio of the apatite/collagen composite to collagen was 97/3 on a mass basis. PBS as concentrated as 10 times was then added until the ion strength of the dispersion became 0.8. The amount of a liquid (pure water+diluted aqueous solution of collagen in phosphoric acid+aqueous NaOH solution+PBS) was 95% by volume of the apatite/collagen composite.

The resultant dispersion was put in a mold, and kept at 37° C. for 2 hours to cause gelation, thereby obtaining a jelly-like molding. This molding was frozen at −20° C., and then dried by a freeze drier to obtain a porous apatite/collagen composite.

(C) Production of Artificial Bone

A porous apatite/collagen composite of 10 mm×10 mm×4 mm was compressed to a sheet-shaped apatite/collagen composite of 10 mm×10 mm×0.3 mm, with pressure of 100 kg/cm$^2$ applied to its surface of 10 mm×10 mm by a monoaxial press at room temperature for 60 seconds.

This apatite/collagen composite sheet was rolled around a rod core of 500 μm in diameter made of Teflon (registered trademark), to obtain a cylindrical body of 10 mm in length, 1.1 mm in diameter with a hollow center portion of 500 μm in diameter. An end of the sheet was press-bonded to the cylindrical body.

16 cylindrical bodies were produced in the same manner as above, bundled such that each had a substantially square transverse cross section, and cross-linked by thermal dehydration at 140° C. to produce an artificial bone constituted by bundled cylindrical bodies.

Examples 2-5

Artificial bones each constituted by a cylindrical body of the apatite/collagen composite having a hollow center portion having the diameter shown in Table 1 were produced in the same manner as in Example 1 except for changing the thickness of a core rod, around which the apatite/collagen composite sheet was rolled.

TABLE 1

| No. | Diameter of Hollow Center Portion (μm) |
|---|---|
| Example 1 | 500 |
| Example 2 | 100 |
| Example 3 | 200 |
| Example 4 | 700 |
| Example 5 | 1000 |

Effect of the Invention

Because the artificial bone of the present invention capable of being absorbed and replaced by an autogenous bone can be implanted in any portion in the body, it is not necessary to use an autogenous bone taken from a patient himself unlike a conventional manner, thereby reducing the burden of a patient needing bone grafting. Further, because an autogenous bone need not be taken even for implanting, the burden of doctors in operation is also reduced. The method of the present invention provides an artificial bone capable of being absorbed and replaced by an autogenous bone, which has similar composition and structure to those of living bones.

The present disclosure relates to subject matter contained in Japanese Patent Application No. 2008-313340 filed on Dec. 9, 2008, which is expressly incorporated herein by reference in its entirety.

What is claimed is:

1. An artificial bone capable of being absorbed and replaced by an autogenous bone, which comprises a plurality of cylindrical bodies bundled in parallel so as to be integrated with each other by rolling a sheet-shaped, porous apatite/ collagen composite around the plurality of bundled cylindrical bodies, each of said cylindrical bodies being obtained by rolling a sheet-shaped, porous apatite/collagen composite, and having a hollow center portion of said cylindrical body penetrating from one end surface to the other end surface having a diameter of 100-1000 μm so as to have excellent penetrability of cells affecting the formation of bones and prevent the intrusion of fibrous tissues resulting in poor bone formation.

2. The artificial bone capable of being absorbed and replaced by an autogenous bone according to claim 1, wherein said sheet-shaped, porous apatite/collagen composite has pores having diameters of 100-1000 μm at a density of 1 or more per 1 cm² formed by punching through a sheet.

3. A method for producing an artificial bone comprising a plurality of cylindrical apatite/collagen composites capable of being absorbed and replaced by an autogenous bone, the method comprising; forming a sheet-shaped, porous apatite/collagen composite, rolling said sheet-shaped, porous apatite/collagen composite into a cylindrical body, bundling a plurality of cylindrical bodies in parallel so as to be integrated with each other, and rolling a sheet-shaped, porous apatite/collagen composite around the plurality of bundled cylindrical bodies.

4. The method according to claim 3, wherein said sheet-shaped, porous apatite/collagen composite is formed by compressing a block-shaped, porous apatite/collagen composite.

5. The method according to claim 3, further comprising providing said sheet-shaped, porous apatite/collagen composite with pores having diameters of 100-1000 μm formed by punching.

6. The method according to claim 3, wherein a plurality of said cylindrical apatite/collagen composites are cross-linked after bundling.

* * * * *